US 8,211,461 B2
Jul. 3, 2012

(12) United States Patent
Burton et al.

(10) Patent No.: US 8,211,461 B2
(45) Date of Patent: Jul. 3, 2012

(54) COMPOSITIONS AND METHODS FOR PROMOTING WEIGHT GAIN AND FEED CONVERSION

(75) Inventors: Graham William Burton, Ottawa (CA); Janusz Daroszewski, Ottawa (CA)

(73) Assignee: Chemaphor Inc., Ottawa, Ontario (CA)

( * ) Notice: Subject to any disclaimer, the term of this patent is extended or adjusted under 35 U.S.C. 154(b) by 1076 days.

(21) Appl. No.: 11/664,047

(22) PCT Filed: Sep. 23, 2005

(86) PCT No.: PCT/CA2005/001458
§ 371 (c)(1),
(2), (4) Date: Feb. 22, 2008

(87) PCT Pub. No.: WO2006/034570
PCT Pub. Date: Apr. 6, 2006

(65) Prior Publication Data
US 2008/0311175 A1   Dec. 18, 2008

Related U.S. Application Data

(60) Provisional application No. 60/613,824, filed on Sep. 28, 2004.

(51) Int. Cl.
A23K 1/17   (2006.01)
(52) U.S. Cl. ...................................... 424/442
(58) Field of Classification Search .................. None
See application file for complete search history.

(56) References Cited

U.S. PATENT DOCUMENTS

| | | | |
|---|---|---|---|
| 3,206,316 A | 9/1965 | Heinrich | |
| 4,105,855 A | 8/1978 | Schulz et al. | |
| 4,127,455 A | 11/1978 | Schulz et al. | |
| 4,333,922 A | 6/1982 | Herschler | |
| 4,351,346 A | 9/1982 | Brummer et al. | |
| 4,642,318 A | 2/1987 | Wolff | |
| 4,889,847 A | 12/1989 | Kligman et al. | |
| 4,996,069 A | 2/1991 | de Hey et al. | |
| 5,084,292 A | 1/1992 | Van Dort et al. | |
| 5,097,063 A | 3/1992 | Moldt | |
| 5,225,604 A | 7/1993 | Moldt | |
| 5,252,604 A | 10/1993 | Nagy et al. | |
| 5,290,605 A | 3/1994 | Shapira | |
| 5,310,554 A | 5/1994 | Haigh | |
| 5,358,915 A | 10/1994 | Nebergall et al. | |
| 5,475,006 A | 12/1995 | Burton et al. | |
| 5,646,186 A | 7/1997 | Wang et al. | |
| 5,665,776 A | 9/1997 | Yu et al. | |
| 5,670,548 A | 9/1997 | Bernhard et al. | |
| 5,719,195 A | 2/1998 | Braiman | |
| 5,744,502 A * | 4/1998 | Lignell et al. ............ 514/725 |
| 5,759,528 A | 6/1998 | Yamada et al. | |
| 5,874,093 A | 2/1999 | Eliaz et al. | |
| 5,965,616 A | 10/1999 | Wang et al. | |
| 5,998,395 A | 12/1999 | Kligman | |
| 6,008,254 A | 12/1999 | Kligman et al. | |
| 6,080,393 A | 6/2000 | Liu et al. | |
| 6,083,520 A * | 7/2000 | Toneby ........................ 424/420 |
| 6,228,887 B1 | 5/2001 | Kligman et al. | |
| 6,251,953 B1 | 6/2001 | Baranowitz | |
| 6,296,877 B1 * | 10/2001 | Auweter et al. ............... 424/490 |
| 6,423,743 B1 | 7/2002 | Romancyzk | |
| 6,433,025 B1 | 8/2002 | Lorenz | |
| 6,544,532 B1 | 4/2003 | Jager-Lezer et al. | |
| 7,132,458 B2 | 11/2006 | Burton et al. | |
| 2002/0088403 A1 | 7/2002 | Heinzl et al. | |
| 2002/0165285 A1 | 11/2002 | Runge et al. | |
| 2005/0249787 A1 | 11/2005 | Reynolds et al. | |
| 2007/0043046 A1 | 2/2007 | Bernardon et al. | |
| 2007/0282010 A1 | 12/2007 | Aberg | |
| 2008/0025929 A1 | 1/2008 | Burton et al. | |
| 2008/0107652 A1 | 5/2008 | Durvasula et al. | |
| 2008/0311175 A1 | 12/2008 | Burton et al. | |
| 2009/0306222 A1 | 12/2009 | Burton et al. | |

FOREIGN PATENT DOCUMENTS

| | | |
|---|---|---|
| CA | 2 171 625 | 2/1996 |
| CA | 2 221 122 | 5/1998 |
| CA | 2357275 | 10/2002 |
| CA | 2455747 | 2/2003 |
| CA | 2474208 | 8/2003 |
| CA | 2495355 | 2/2004 |
| CN | 1131939 A | 9/1996 |
| CN | 1505602 A | 6/2004 |
| EP | 0385335 | 9/1990 |
| EP | 0 415 464 A2 | 3/1991 |
| EP | 0 399 619 B1 | 12/1994 |
| EP | 0 630 578 A2 | 12/1994 |
| EP | 0 718 284 A2 | 6/1996 |
| EP | 1 186 245 A2 | 3/2002 |
| EP | 1 253 131 A1 | 10/2002 |
| GB | 1021537 | 3/1966 |
| GB | 1 323 800 | 7/1973 |

(Continued)

OTHER PUBLICATIONS

"Polysorbate 80" from Wikipedia (pp. 1-4) retrieved online on Sep. 21, 2011 (http://en.wikipedia.org/wiki/Polysorbate_80).*
Database Biosis, PREV200300291110, "Addition of Beta-Ionone to the Diet Fails to Affect Growth Performance in Female Broiler Chickens," Apr. 21, 2003.
European Search Report for PCT/CA2005/001458 mailed on Feb. 14, 2008.
International Search Report for PCT/CA2005/001458 mailed on Jan. 3, 2006.
U.S. Appl. No. 08/527,039, filed Sep. 12, 1995, Burton et al.
Alaoui-Jamali et al., "In Vivo Reversal of Doxorubicin Resistance by a New Tiapamil Analog Ro11-2933," *J. Pharmacol. Exp. Ther.* 264:1299-1304 (1993).

(Continued)

*Primary Examiner* — Bethany Barham
(74) *Attorney, Agent, or Firm* — Clark & Elbing LLP; Kristina Bieker-Brady

(57) ABSTRACT

The invention features compositions for administration of an oxidatively transformed carotenoid or a component thereof and methods of promoting weight gain and feed conversion efficiency therewith.

28 Claims, No Drawings

FOREIGN PATENT DOCUMENTS

| GB | 1 502 895 | 3/1978 |
|---|---|---|
| JP | 6-197703 A | 7/1994 |
| JP | 6-276956 | 10/1994 |
| RU | 2211048 C1 | 8/2003 |
| WO | WO 93/15740 | 8/1993 |
| WO | WO 96/05160 | 2/1996 |
| WO | WO 96/34601 | 11/1996 |
| WO | WO 98/44808 | 10/1998 |
| WO | WO 99/30701 | 6/1999 |
| WO | WO 01/10901 | 2/2001 |
| WO | WO 01/24787 | 4/2001 |
| WO | WO 02/085831 | 10/2002 |
| WO | WO 03/013268 | 2/2003 |
| WO | WO 03/066583 | 8/2003 |
| WO | WO 2004/016099 | 2/2004 |
| WO | WO 2005/079143 | 9/2005 |
| WO | WO 2006/034570 | 4/2006 |
| WO | WO 2006/120565 | 11/2006 |
| WO | WO 2007/043046 | 4/2007 |
| WO | WO 2007/112587 | 10/2007 |
| WO | WO 2009/052629 | 4/2009 |
| WO | WO 2010/124391 | 11/2010 |
| WO | WO 2010/124392 | 11/2010 |
| WO | WO 2011/103464 | 8/2011 |

OTHER PUBLICATIONS

Alija et al., "Cytotoxic and Genotoxic Effects of Beta-Carotene Breakdown Products on Primary Rat Hepatocytes," *Carcinogenesis* 25:827-831 (2004).
Anon, "Chemaphor Announces Positive Results of Pilot Canine Clinical Trial of an Oximunol™ Supplement," Medical News Today, Feb. 2, 2010 (available at www.medicalnewstoday.com/articles/177855.php).
Anon, "Vitamin A, Tumor Initiation and Tumor Protection," *Nutr. Rev.* 37:153-156 (1979).
Blount et al., "Carotenoid Modulation of Immune Function and Sexual Attractiveness in Zebra Finches," *Science* 300:125-127 (2003).
Brooks et al., "Recent Developments in the Chemistry, Biochemistry, Geochemistry and Post-Tetrad Ontogeny of Sporopollenins Derived from Pollen and Spore Exines," in *Pollen Development and Physiology*, pp. 99-114 (ed. J. Heslop-Harris, Butterworths, London 1971).
Brouwer et al., "A New Synthesis of 4-OR*-3-penten-1-ynes ($C_5$-Fragment) as a Tool for the Preparation of Vitamin A," *J. of the Royal Netherlands Chem. Soc.* 98:316-320 (1979).
Burton et al., "Beta-Carotene: An Unusual Type of Lipid Antioxidant," *Science* 224:569-573 (1984).
Chew, "Role of Carotenoids in the Immune Response," *J. Dairy Sci.* 76:2804-2811 (1993).
Clark et al., "Retinoic Acid Oxidation at High Oxygen Pressures: Evidence for Spin-Forbidden Direct Addition of Triplet Molecular Oxygen," *J. Am. Chem. Soc.* 119:9560-9561 (1997).
Deming et al., "Mammalian Carotenoid Absorption and Metabolism," *Pure Appl. Chem.* 71:2213-2223 (1999).
El-Tinay et al., "Oxidation of Beta-Carotene. Site of Initial Attack," *J. Org. Chem.* 35:2290-2293 (1970).
Giuliani et al., "Preliminary Observations with an Ointment Containing Tretinoin (Retinoic Acid), Salicylic Acid, Sulfur, Betamethasone, Camphor and Allantoin in Hyperkeratotic Dermatosis," *Chronica Dermatologica* 5:581-594 (1974).
Hardman, "Goodman & Gilman's The Pharmacological Basis of Therapeutics," pp. 51, 57, and 58 (9$^{th}$ edition, McGraw-Hill, 1996).
Hill et al., "Retinoids and Cancer Prevention," *Annu. Rev. Nutr.* 12:161-181 (1992).
Hong et al., "Recent Advances in Chemoprevention of Cancer," *Science* 278:1073-1077 (1997).
Hoskinson et al., "Age-Related Changes in Mitogen-Induced Lymphocyte Proliferation and Polymorphonuclear Neutrophil Function in the Piglet," *J. Anim. Sci.* 68:2471-2478 (1990).
Hunter et al., "The Oxidation of Beta-Carotene in Solution by Oxygen," *J. Chem. Soc.* Jan:1-4 (1947).
Kanasawud et al., "Mechanism of Formation of Volatile Compounds by Thermal Degradation of Cartenoids in Aqueous Medium. 2. Lycopene Degradation," *J. Agric. Food Chem.* 38:1238-1242 (1990).
Kiefer et al., "Identification and Characterization of a Mammalian Enzyme Catalyzing the Asymmetric Oxidative Cleavage of Provitamin A," *J. Biol. Chem.* 276:14110-14116 (2001).
Kim et al., "Dietary Lutein Stimulates Immune Response in the Canine," *Vet. Immunol. Immunopathol.* 74:315-327 (2000).
Krinsky, "Actions of Carotenoids in Biological Systems," *Annu. Rev. Nutr.* 13:561-587 (1993).
Lee et al., "Addition of Beta-Ionone to the Diet Fails to Affect Growth Performance in Female Broiler Chickens," *Anim. Feed Sci. Technol.* 106:219-223 (2003).
Martin et al., "Chemistry of Carotenoid Oxidation and Free Radical Reactions," *Pure Appl. Chem.* 71:2253-2262 (1999).
Marty et al., "Degradation of Trans-Beta-Carotene During Heating in Sealed Glass Tubes and Extrusion Cooking," *J. Food. Sci.* 51:698-702 (1986).
Marty et al., "Degradation Products of Trans-Beta-Carotene Produced During Extrusion Cooking," *J. Food. Sci.* 53:1880-1886 (1988).
Mathews-Roth, "Carotenoids and Cancer Prevention: Experimental and Epidemiological Studies," *Pure Appl. Chem.* 57:717-722 (1985).
Mordi et al., "Exploratory Study of Beta-Carotene Autoxidation," *Tetrahedron Lett.* 32:4203-4206 (1991).
Mordi et al., "Oxidative Degradation of Beta-Carotene and Beta-Apo-8'-Carotenal," *Tetrahedron* 49:911-928 (1993).
Morganti et al., "Protective Effects of Oral Antioxidants on Skin and Eye Function," *SKINmed.* 3:310-316 (2004).
Onyewu et al., "Characterization of Beta-Carotene Thermal Degradation Products in a Model Food System," *J. Am. Oil Chem. Soc.* 63:1437-1441 (1986).
Oyler et al., "Characterization of Autooxidation Products of Retinoid Acid," *Tetrahedron* 45:7679-7694 (1989).
Peto et al., "Can Dietary Beta-Carotene Materially Reduce Human Cancer Rates?" *Nature* 290:201-208 (1981).
Ramos-Gomez et al., "Sensitivity to Carcinogenesis is Increased and Chemoprotective Efficacy of Enzyme Inducers is Lost in nrf2 Transcription Factor-Deficient Mice," *Proc. Natl. Acad. Sci. USA* 98:3410-3415 (2001).
Rudnic et al., "Oral Solid Dosage Forms," in *Remington: The Science & Practice of Pharmacy*, pp. 856-861 (ed. Alfonso R. Gennaro, 20$^{th}$ edition, Williams & Wilkins, 2000).
Russell, "The Enigma of Beta-Carotene in Carcinogenesis: What Can Be Learned from Animal Studies," *J. Nutr.* 134:262S-268S (2004).
Sciarra et al., "Aerosols," in *Remington: The Science & Practice of Pharmacy*, p. 963 (ed. Alfonso R. Gennaro, 20$^{th}$ edition, Williams & Wilkins, 2000).
Talalay, "Chemoprotection Against Cancer by Induction of Phase 2 Enzymes," *BioFactors* 12:5-11 (2000).
Talalay et al., "Importance of Phase 2 Gene Regulation in Protection Against Electrophile and Reactive Oxygen Toxicity and Carcinogenesis," *Adv. Enzyme Regul.* 43:121-134 (2003).
Trosko et al., "Gap Junctions as Targets for Cancer Chemoprevention and Chemotherapy," *Curr. Drug Targets* 3:465-482 (pp. 1-17) (2002).
Verma et al., "Inhibition of Skin Tumor Promotion by Retinoic Acid and Its Metabolite 5,6-Epoxyretinoic Acid," *Cancer Res.* 40:2367-2371 (1980).
Wang, "Can Smoke-Exposed Ferrets be Utilized to Unravel the Mechanisms of Action of Lycopene?" *J. Nutr.* 135:2053S-2056S (2005).
Communication from the European Patent Office for application No. EP 05 736 675.9 (mail date Feb. 2, 2010, 5 pages).
Iwan'ska et al., "Carotenoids Content of Green Forages and Preserved Feeds," *Acta Acad. Agri. Ac Tech. Olstenensis Zootechnica* 47:117-128 (1997) (Abstract only) (2 pages).
Supplementary European Search Report for EP 05736675, dated Sep. 18, 2009 (3 pages).
International Preliminary Report on Patentability for PCT/CA2005/001458, dated Feb. 7, 2007 (6 pages).

\* cited by examiner

COMPOSITIONS AND METHODS FOR PROMOTING WEIGHT GAIN AND FEED CONVERSION

CROSS-REFERENCE TO RELATED APPLICATIONS

This application is the U.S. National Stage of International Application No. PCT/CA2005/001458, filed Sep. 23, 2005, which claims benefit of the U.S. Provisional Application No. 60/613,824, filed Sep. 28, 2004.

BACKGROUND OF THE INVENTION

The invention relates to the use of carotenoid oxidation products to promote growth and feed conversion.

Animals raised under modern conditions optimized for growth promotion receive rations containing high proportions of protein, usually in the form of soybean or cottonseed meal, and high percentages of grains such as corn or milo, a type of sorghum. Feed additives which have been used include such hormones as diethylstilbestrol, or DES which also increases the rate of weight gain, and tranquilizers that prevent the disease or weight loss brought on by stressful confinement conditions. Routine antibiotic administration to animals has become almost universal since the discovery that the addition of small amounts of antibiotics such as penicillin, tetracycline and sulfamethazine, to animal feed increases the growth of pigs and cattle. Because feed is a relatively expensive cost factor in the production of food from animals (typically 50 to 70% of the cost), any improvement in the ability of the animal to convert feed into food products or enhancement in growth rate can directly improve the profitability of a food producer.

The use of such additives has not been without problems. One of the hormones that was commonly used as a growth stimulant, diethylstilbestrol, has been shown to be a carcinogen and has been banned from further use in most countries. Furthermore, the widespread use of antibiotics in animal feed promotes the development of antibiotic-resistant microorganisms.

As a result of the increasing appearance of antibiotic-resistant bacteria in feed lots and the potential for epidemics caused by antibiotic resistant bacteria, there is increasing governmental pressure to limit the use of antibiotics in animal feed. Consequently, there is an immediate and increasing need for new, safe, and effective growth stimulators of farm animals. There is a also a need for a method of improving the ability of animals to more efficiently convert their feed to body weight or other edible products.

SUMMARY OF THE INVENTION

In a first aspect, the invention features a foodstuff including oxidatively transformed carotenoid or a component thereof. The foodstuff can include from 0.00001% to 0.1% (w/w) oxidatively transformed carotenoid. Desirably, the foodstuff contains oxidatively transformed carotenoid in an amount between 0.00001% and 0.05%, 0.00001% and 0.01%, 0.00001% and 0.005%, 0.00001% and 0.001%, 0.00001% and 0.0005%, or 0.00001% and 0.0001% (w/w). The foodstuff can include from 0.0000001% to 0.001% (w/w) of a component of oxidatively transformed carotenoid. Desirably, the foodstuff contains a component of oxidatively transformed carotenoid in an amount between 0.0000001% and 0.0005%, 0.0000001% and 0.0001%, 0.0000001% and 0.00005%, 0.0000001% and 0.00001%, 0.0000001% and 0.000005%, or 0.0000001% and 0.000001% (w/w).

In a second aspect, the invention features a method of promoting weight gain in an animal by administering to the animal oxidatively transformed carotenoid or a component thereof in an amount effective to promote weight gain.

In a third aspect, the invention features a method of increasing feed conversion efficiency in an animal by administering to the animal oxidatively transformed carotenoid or a component thereof in an amount effective to increase feed conversion efficiency.

In a fourth aspect, the invention features a kit, including: (i) a composition including oxidatively transformed carotenoid or a component thereof; and (ii) instructions for administering the composition to an animal to promote weight gain or increase feed conversion efficiency.

In a fifth aspect, the invention features a method for making a foodstuff including oxidatively transformed carotenoid or a component thereof, said method comprising the steps of (i) preparing oxidatively transformed carotenoid or a component thereof and (ii) mixing the oxidatively transformed carotenoid or a component thereof with a foodstuff.

In an embodiment of any of the aspects described herein, the oxidatively transformed carotenoid is used without fractionation of the mixture. Alternatively, a composition including the polymeric component of oxidatively transformed carotenoid or a composition including 2-methyl-6-oxo-2,4-heptadienal, dihydroactinidiolide, $\beta$-cyclocitral, $\beta$-ionone, $\beta$-ionone 5,6-epoxide, 4-oxo-$\beta$-ionone, $\beta$-ionylidene acetaldehyde, $\beta$-ionylidene acetaldehyde 5,6-epoxide, 4-oxo-$\beta$-ionylidene acetaldehyde, $\beta$-apo-13-carotenone, $\beta$-apo-13-carotenone 5,6-epoxide, 4-oxo-$\beta$-apo-13-carotenone, retinal, retinal 5,6-epoxide, or mixtures thereof can be used in the methods, kits, and foodstuffs of the invention. administered to said animal. Desirably, the component of oxidatively transformed carotenoid used includes the polymeric component and/or 2-methyl-6-oxo-2,4-heptadienal.

In another embodiment of any of the aspects described herein, the animal is selected from humans, dogs, cats, horses, sheep, swine, cattle, poultry, and fish.

In an embodiment of any of the above methods, oxidatively transformed carotenoid or a component thereof, respectively, is administered orally, by injection, or by aerosol. Desirably, the oxidatively transformed carotenoid or a component thereof is admixed with a foodstuff and fed to the animal.

Foodstuffs of the invention include, without limitation, baked goods, beverages, beverage mixes, health bars, biscuits, and animal feeds. The animal feed may be a dry or semi-moist pet food, or feed for an agricultural animal, such as horse feed, swine feed (e.g., nursery/starter swine feed, grow-finish swine feed, or breeding herd swine feed), poultry feed (e.g., turkey poultry feed, broilers poultry feed, or breeders poultry feed), sheep feed, cattle feed (e.g., dairy cattle feed or beef cattle feed), or fish feed (e.g., tilapia feed, catfish feed, trout feed, or salmon feed).

Foodstuffs of the invention may further include an antioxidant. Exemplary antioxidants include, without limitation, beta-carotene, vitamin E, vitamin C, butylated hydroxytoluene, butylated hydroxyanisole, tertiary-butylhydroquinone, propyl gallate, and ethoxyquin.

In another embodiment of any of the above aspects, the foodstuffs of the invention further include a medicament, such as an antibiotic or hormone. Such medicaments can be added in amounts typically found in commercial feeds.

As used herein, an "amount effective to promote weight gain" is an amount of oxidatively transformed carotenoid or a component thereof which causes an animal to gain weight faster in comparison to an animal of the same species and age which is raised under the same conditions and receives the same diet without oxidatively transformed carotenoid or a component thereof. The average increase in mass is greater than 0.5%, preferably greater than 1%, 2%, 3%, 4%, or even 5% in comparison to the control animal.

As used herein, an "amount effective to increase feed conversion efficiency" is an amount of oxidatively transformed carotenoid or a component thereof which causes an increase feed conversion efficiency in comparison to an animal of the same species and age which is raised under the same conditions and receives the same diet without oxidatively transformed carotenoid or a component thereof. The average reduction in feed needed to produce the same weight is greater than 0.5%, preferably greater than 1%, 2%, 3%, 4%, or even 5% in comparison to the control animal.

By "animal" is meant any animal including, without limitation, humans, dogs, cats, horses, sheep, swine, cattle, poultry, and fish.

As used herein, "carotenoid" refers to naturally-occurring pigments of the terpenoid group that can be found in plants, algae, bacteria, and certain animals, such as birds and shellfish. Carotenoids include carotenes, which are hydrocarbons (i.e., without oxygen), and their oxygenated derivatives (i.e., xanthophylls). Examples of carotenoids include lycopene; beta-carotene; zeaxanthin; echinenone; isozeaxanthin; astaxanthin; canthaxanthin; lutein; citranaxanthin; β-apo-8'-carotenic acid ethyl ester; hydroxy carotenoids, such as alloxanthin, apocarotenol, astacene, astaxanthin, capsanthin, capsorubin, carotenediols, carotenetriols, carotenols, cryptoxanthin, decaprenoxanthin, epilutein, fucoxanthin, hydroxycarotenones, hydroxyechinenones, hydroxylycopene, lutein, lycoxanthin, neurosporine, phytoene, phytofluoene, rhodopin, spheroidene, torulene, violaxanthin, and zeaxanthin; and carboxylic carotenoids, such as apocarotenoic acid, β-apo-8'-carotenoic acid, azafrin, bixin, carboxylcarotenes, crocetin, diapocarotenoic acid, neurosporaxanthin, norbixin, and lycopenoic acid.

As used herein "oxidatively transformed carotenoid" refers to a carotenoid which has been reacted with up to 6 to 8 molar equivalents of oxygen, or an equivalent amount of oxygen from another oxidizing agent, resulting in a mixture of very low molecular weight oxidative cleavage products and a large proportion of polymeric material (i.e., that component of the oxidatively transformed carotenoid having a molecular weight of greater than 1,000 Daltons). The resulting reaction produces a mixture that includes molecular species having molecular weights ranging from about 100 to 8,000 Daltons. The polymeric material is believed to be formed by the many possible chemical recombinations of the various oxidative fragments that are formed. Methods of making oxidatively transformed carotenoid are described in U.S. Pat. No. 5,475,006 and U.S. Ser. No. 08/527,039, each of which are incorporated herein by reference.

As used herein "component" refers to an active oxidized component of an oxidatively transformed carotenoid mixture that includes either polymeric material or a compound selected from 2-methyl-6-oxo-2,4-heptadienal, dihydroactinidiolide, β-cyclocitral, β-ionone, β-ionone 5,6-epoxide, 4-oxo-β-ionone, β-ionylidene acetaldehyde, β-ionylidene acetaldehyde 5,6-epoxide, 4-oxo-β-ionylidene acetaldehyde, β-apo-13-carotenone, β-apo-13-carotenone 5,6-epoxide, 4-oxo-β-apo-13-carotenone, retinal, and retinal 5,6-epoxide; and mixtures thereof. Components of oxidatively transformed carotenoid are active in that they are capable of either increasing feed conversion efficiency in an animal or promoting weight gain in an animal, or both. Methods for assessing whether a particular fraction of oxidatively transformed carotenoid is capable of are increasing feed conversion efficiency or promoting weight gain are provided in the Examples. Methods of fractionating oxidatively transformed carotenoid mixtures into components are described in U.S. Pat. No. 5,475,006 and U.S. Ser. No. 08/527,039, each of which are incorporated herein by reference.

The synthesis and purification of 2-methyl-6-oxo-2,4-heptadienal has been reported in U.S. Ser. No. 08/527,039. A more convenient five-step synthetic scheme for the preparation of 2-methyl-6-oxo-2,4-heptadienal is provided in U.S. Ser. No. 10/196,695, published May 22, 2003.

The compositions and methods of the invention can be used to promote weight gain and increase feed conversion efficiency in animals.

Other features and advantages of the invention will be apparent from the following Detailed Description and the claims.

DETAILED DESCRIPTION

The invention provides compositions for the administration of oxidatively transformed carotenoid and components thereof. The compositions can be useful for weight gain and feed conversion efficiency in animals.

Administration

The oxidatively transformed carotenoid or a component thereof is administered in an amount effective to promote weight gain or effective to increase feed conversion efficiency. For oxidatively transformed carotenoid, typical dose ranges are from about 5 µg/kg to about 50 mg/kg of body weight per day. Desirably, a dose of between 5 µg/kg and 5 mg/kg of body weight, or 5 µg/kg and 0.5 mg/kg of body weight, is administered. For a component of oxidatively transformed carotenoid, typical dose ranges are from about 0.05 µg/kg to about 500 µg/kg of body weight per day. Desirably, a dose of between 0.05 µg/kg and 50 µg/kg of body weight, or 0.05 µg/kg and 5 µg/kg of body weight, is administered. The dosage of oxidatively transformed carotenoid or a component thereof to be administered is likely to depend on such variables as the species, diet, and age of the animal. Standard trials, such as those described in Example 1 may be used to optimize the dose and dosing frequency of the oxidatively transformed carotenoid or a component thereof.

Oxidatively transformed carotenoid or a component thereof may be administered orally, by injection, or by aerosol. When injected, the administration can be parenteral, intravenous, intra-arterial, subcutaneous, intramuscular, intracranial, intraorbital, intraventricular, intracapsular, intraspinal, intracisternal, or intraperitoneal.

Oxidatively transformed carotenoid or a component thereof may be added to a foodstuff or formulated with a pharmaceutically acceptable diluent, carrier, or excipient as described in U.S. Ser. No. 10/196,695, published May 22, 2003. Pharmaceutical formulations may, for example, be in the form of liquid solutions or suspensions; for oral administration, formulations may be in the form of tablets or capsules; and for intranasal formulations, in the form of powders, nasal drops, or aerosols. Methods well known in the art for making formulations are found, for example, in "Remington: The Science and Practice of Pharmacy" (20th ed., ed. A. R. Gennaro, 2000, Lippincott Williams & Wilkins).

Desirably, oxidatively transformed carotenoid or a component thereof is admixed with a foodstuff and fed to the animal.

Foodstuffs

Oxidatively transformed carotenoid or a component thereof can be admixed with a foodstuff and fed to the animal in an amount effective to promote weight gain or effective to increase feed conversion efficiency.

In preparing a foodstuff of the invention, the oxidatively transformed carotenoid or a component thereof is optionally admixed with a bulking agent prior to being added to the foodstuff. Bulking agents include, without limitation, starch, protein, fats, and mixtures thereof. Desirably, the bulking agent is selected from corn starch, whey, flour, sugar, soybean meal, maltodextrin, and guar gum.

Foodstuffs of the invention can also include antioxidants to prevent further oxidation of the oxidatively transformed carotenoid or a component thereof. Oxidation can be prevented by the introduction of naturally-occurring antioxidants, such as beta-carotene, vitamin E, vitamin C, and tocopherol or of synthetic antioxidants such as butylated hydroxytoluene, butylated hydroxyanisole, tertiary-butylhydroquinone, propyl gallate or ethoxyquin to the foodstuff. The amount of antioxidants incorporated in this manner depends on requirements such as product formulation, shipping conditions, packaging methods, and desired shelf-life.

Animal Feeds

Animal feeds of the present invention will always contain oxidatively transformed carotenoid or a component thereof in an amount effective to increase weight gain and/or feed conversion. The animal feeds are generally formulated to provide nutrients in accordance with industry standards. The feeds may be formulated from a variety of different feed ingredients, which are chosen according to market price and availability. Accordingly, some components of the feed may change over time. For discussions on animal feed formulations and NRC guidelines, see Church, Livestock Feeds and Feeding, O&B Books, Inc., Corvallis Oreg. (1984) and Feeds and Nutrition Digest, Ensminger, Oldfield and Heineman eds., Ensminger Publishing Corporation, Clovis, Calif. (1990), each of which is incorporated herein by reference.

Swine and other animal feeds are traditionally balanced based upon protein and energy requirements, and then adjusted if needed to meet the other requirements, which will vary for the different stages of growth and maintenance of the animal. Growing young animals will require higher protein feeds, while finishing animals close to market will require higher energy, high carbohydrate, feeds. For example, typical hog prestarter, starter and grower-finisher feeds will generally contain about 20-24% protein, 18-20% protein and 13-17% protein respectively. In some feeding situations, care must be taken to provide the appropriate amino acids as well as overall protein content. For example, hogs fed large amounts of corn must have adequate lysine made available in the feed. In most animal diets, energy requirements are met by starches in cereal grains. Energy requirements may also be met by addition of fat to the feed. Animal feeds containing oxidatively transformed carotenoid or a component thereof may also be formulated for dogs, cats, poultry, fish, and cattle, among others.

Other ingredients may be added to the animal feed as needed to promote the health and growth of the animal. The ingredients include, without limitation, sugars, complex carbohydrates, amino acids (e.g., arginine, histidine, isoleucine, leucine, lysine, methionine, phenylalanine, threonine, tryptophan, valine, tyrosine, alanine, aspartic acid, sodium glutamate, glycine, proline, serine, and cysteine, among others), vitamins (e.g., thiamine, riboflavin, pyridoxine, niacin, niacinamide, inositol, choline chloride, calcium pantothenate, biotin, folic acid, ascorbic acid, and vitamins A, B, K, D, E, among others), minerals, protein (e.g., meat meal, fish meal, liquid or powdered egg, fish solubles, whey protein concentrate), oils (e.g., soybean oil), cornstarch, calcium, inorganic phosphate, copper sulfate, and sodium chloride. Any medicament ingredients known in the art may also be added to the animal feed, including, without limitation, antibiotics and hormones. For vitamin, mineral and antibiotic supplementation of animal feeds see Church, Livestock Feeds and Feeding, O&B Books, Inc., Corvallis Oreg. (1984).

Any animal feed blend known in the art can be used in accordance with the present invention, including, without limitation, forages, such as orchard grass, timothy, tall fescue, ryegrass, alfalfa, sainfoin, clovers and vetches, grain feeds, such as corn, wheat, barley sorghum, triticale, rye, canola, and soya beans, crop residues, cereal grains, legume by-products, and other agricultural by-products. In situations where the resulting feed is to be processed or preserved, the feed may be treated with oxidatively transformed carotenoid or a component thereof before processing or preservation. Desirably, the animal feed of the invention includes rapeseed meal, cottonseed meal, soybean meal, or cornmeal.

Processing may include drying, ensiling, chopping, pelleting, cubing, baling, rolling, tempering, grinding, cracking, popping, extruding, micronizing, roasting, flaking, cooking, and/or exploding. For example, pelleted feed is created by first mixing feed components and then compacting and extruding the feed components through a die with heat and pressure. Animal feeds of the invention can be pelleted as described in, for example, MacBain, Pelleting Animal Feed, American Feed Manufacturers Association, Arlington, Va. (1974), incorporated herein by reference.

Baked Goods and Beverages

Foodstuffs of the invention can be in the form of a health bar, preferably supplied in foil or other types of wrappers, as is commonly seen in most food markets, convenience stores and health food stores. Typically, such health bars are commonly made by a machine extrusion process that extrudes the mixed ingredients into the desired size and shape bar, which is then conveyed to automatic wrapping machinery. Health bars may be baked, rather than extruded.

The foodstuff may also be extruded, baked, rolled, pressed, cut or otherwise formed into bars or baked goods, such as cookies, brownies, cakes or muffins. In the manufacturing process for bars that are extruded, ingredients such as glycerine, lecithin, vegetable and other oils (such as sunflower oil) are used in part to help bind ingredients together so as to help form a uniformly shaped bar in the extrusion machinery. Such known processes can be used to produce the health bars and baked goods of the present invention.

Foodstuffs of the invention can be in the form of a ready-to-drink beverage, requiring no addition of water and/or mixing with water or other liquids, or a powder or a liquid concentrate that is mixed with water, fruit juice, fruit and/or other flavored drinks, and/or fruit drink concentrates to make, for example, a flavored beverage, or with milk to make a drink having a character similar to that of a milk-shake.

The following examples are put forth so as to provide those of ordinary skill in the art with a complete disclosure and description of how the methods and compositions claimed herein are performed, made, and evaluated, and are intended to be purely exemplary of the invention and are not intended to limit the scope of what the inventors regard as their invention.

EXAMPLE 1

Effect of Oxidatively Transformed Carotenoid on Growth and Feed Conversion in Pigs Two groups of 48 weaned pigs, ages 18-21 days old, were used to analyze the effects of oxidatively transformed carotenoid as a food additive on growth and feed conversion.

The first 48 pigs were randomly distributed into 16 pens (3 pigs per pen) divided equally between two temperature-controlled rooms. All 24 pigs in one room were injected with an attenuated vaccine against Porcine Respiratory and Reproductive Syndrome (Vaccinated room) and the other 24 pigs were injected a placebo of saline solution (Control room).

Two pens per room were randomly assigned to one of four diets consisting of oxidatively transformed beta-carotene (OxBC) admixed with commercial swine feed.

OxBC was prepared as follows. A suspension of beta-carotene in ethyl acetate at room temperature was saturated with oxygen by bubbling the gas through it while stirring the mixture. After 8 days, when 6 to 8 molar equivalents of oxygen had been consumed, the solvent was evaporated to give a yellow residue of OxBC.

OxBC was mixed with 3 to 10 equivalents by weight of corn starch and ground in a mortar until a homogenous product (by visual inspection) was obtained. The resulting freely flowing powder was further diluted by simple mixing with corn starch and subsequently mixed with a powdered commercial swine feed, the components were milled together, and the mixture pressed into pellets.

The four diets used in the study, diets A-D below, contained OxBC at levels of 0, 10, 30, and 100 mg/kg of swinefeed.

| | |
|---|---|
| Diet A (Control): | Commercial diet with no OxBC |
| Diet B: | Commercial diet with 0.001% (w/w) OxBC |
| Diet C: | Commercial diet with 0.003% (w/w) OxBC |
| Diet D: | Commercial diet with 0.010% (w/w) OxBC |

The pigs had Ad-libitum access to feed and water during the 4-week trial. After a 4 day acclimatization, pigs were individually weighed and placed on the experimental diets for four weeks. Piglets were weighed every 7 days following placement on the diets. All feed given to the pigs was weighed daily, and once per week the feeders were emptied and the feed inventory was weighed.

A sequential replicate of this study was performed. The data were analyzed using a mixed model linear regression with pen as a random effect and start weight as a covariate using software developed by Stata corp.

The growth rate of the pigs was calculated by subtracting the start weight of the pigs from the final weight and dividing by the number of days on the study. These data are summarized in Table 1.

TABLE 1

| OxBC level | Average Daily Gain (kg ± SE) |
|---|---|
| 0% (w/w) Diet A (control) | 0.535 ± 0.019 |
| 0.001% (w/w) Diet B | 0.578 ± 0.019 |
| 0.003% (w/w) Diet C | 0.540 ± 0.020 |
| 0.010% (w/w) Diet D | 0.507 ± 0.019 |

There was an improvement in growth rate associated with feeding the OxBC product for four weeks after weaning. The effect was statistically significant at 0.001% (w/w) OxBC, where the pigs grew approximately 8% faster than the untreated controls.

The feed conversion was calculated as the weight of the feed consumed in a pen (3 pigs) divided by the weight gained by all three pigs during the study period. These data are summarized in Table 2.

TABLE 2

| OxBC level | Feed Conversion (kg feed/kg pork ± SE) |
|---|---|
| 0% (w/w) Diet A (control) | 1.65 ± 0.035 |
| 0.001% (w/w) Diet B | 1.51 ± 0.035 |
| 0.003% (w/w) Diet C | 1.63 ± 0.035 |
| 0.010% (w/w) Diet D | 1.56 ± 0.035 |

The feed conversion efficiency of pigs fed for 4 weeks after weaning was increased by the addition of OxBC to the diet. The effect was most pronounced at 0.001% (w/w) OxBC, where the pigs ate approximately 8.5% less feed to gain the same weight.

EXAMPLE 2

Effects of Oxidatively Transformed Carotenoid on Growth Performance in Broiler Chickens Ross×Ross 308 cockerels were obtained from a commercial hatchery. Extra chicks were placed on the 0 ppm control diet in a separate pen for early mortality replacement. Chicks were vaccinated for Marek's Disease (¼ dose per chick), and Infectious Bronchitis at the hatchery. Chicks were not vaccinated for Coccidiosis. Birds which had obvious health problems were excluded from the study.

A total of 1600 chicks were assigned to treatments at arrival. There were 8 blocks in the study, each comprised of 4 pens. Pens within block were randomly and equally assigned to the treatments (A, B, C, D). There were 50 birds per pen and each pen within a block contained birds of similar initial bodyweight. A randomized complete block design was used to study the effects of the following four treatments in a randomized complete block design:

| | |
|---|---|
| Diet A (Control): | Commercial diet with no OxBC |
| Diet B: | Commercial diet with 0.0005% (w/w) OxBC |
| Diet C: | Commercial diet with 0.001% (w/w) OxBC |
| Diet D: | Commercial diet with 0.003% (w/w) OxBC |

Treatment diets were introduced on Day 0 and were fed continuously until study termination on Day 38. Water was provided ad libitum to birds throughout the trial.

In order to manufacture final feeds, the 20% OxBC cornstarch premix (prepared as described in example 1) was diluted with corn starch to produce a 2% (w/w) OxBC premix, with a 0.5% (w/w) free flow agent (Sipernat; Silicon dioxide), and 1% mineral oil. The required amount of active ingredient was delivered by varying the amount of 2% OxBC premix per tonne complete feed (starter feed, grower feed, and finisher feed; Yantzi's Feed & Seed (Tavistock); manufactured as meal).

Experimental feeds were manufactured using standard procedures. In order to minimize cross contamination risk, feeds were manufactured in order of Treatment code (A, B, C, D).

Pen live weights were recorded on Day 0, 18, 31 and 38 days of age. Pen feed consumption were recorded for periods between days 0-18, 18-31, and 31-38 days of age.

The live weight of birds fed OxBC were significantly higher at day 18 ($P=0.010$), day 31 ($P<0.0001$), and at the termination of the trial on day 38 ($P=0.022$) (see Table 3). No significant differences ($P>0.05$) were noted between birds fed 5, 10, or 30 ppm OxBC. Birds were 3.7%, 3.0%, and 4.3% heavier after 38 days of feeding 5, 10, and 30 ppm OxBC, respectively, relative to birds fed the control diet.

Feed conversion ratios (FCR) were not significantly (P=0.572) affected over the starter feed period (day 0 to 18). While the FCR of birds fed 10 and 30 ppm were numerically lower than controls, the relative difference was less than 1% (see Table 3). Feed conversion ratios tended (P=0.053) to be significantly improved in birds fed 5 ppm OxBC over the grower period (days 18-31), but not in those fed 10 or 30 ppm OxBC relative to controls. The relative improvement in feed conversion in birds fed 5 ppm OxBC was 3.4%. In contrast, the FCRs were not significantly different among treatments in the finisher period (day 31 to 38; P=0.803), nor over the entire duration of the trial (day 0 to 38; P=0.242). FCRs were similar among all treatments over the entire study despite birds fed OxBC being significantly heavier at the termination of the trial relative to those fed the control diet.

TABLE 3

|  | Mean body weight (kg) | | | | Feed conversion ratio (kg/kg gain) | | | |
| --- | --- | --- | --- | --- | --- | --- | --- | --- |
|  | Day 0 | Day 18 | Day 31 | Day 38 | D 0-18 | D 18-31 | D 31-38 | D 0-38 |
| 0 ppm control | 0.040 | 0.544 | 1.468 | 2.100 | 1.483 | 1.766 | 2.187 | 1.815 |
| 5 ppm OxBC | 0.040 | 0.575 | 1.553 | 2.178 | 1.484 | 1.706 | 2.224 | 1.792 |
| 10 ppm OxBC | 0.040 | 0.575 | 1.544 | 2.165 | 1.469 | 1.776 | 2.218 | 1.819 |
| 30 ppm OxBC | 0.040 | 0.580 | 1.560 | 2.191 | 1.470 | 1.744 | 2.230 | 1.809 |
| P value | 0.999 | 0.010 | 0.000 | 0.022 | 0.572 | 0.053 | 0.803 | 0.242 |
| Pooled SEM | 0.000 | 0.008 | 0.012 | 0.020 | 0.010 | 0.018 | 0.033 | 0.010 |

The average daily feed intake of birds was significantly improved (P=0.001) over the starter period in birds fed OxBC, with a mean improvement of 5.8% relative to birds fed the control diet (see Table 4). No differences were noted between birds fed 5, 10 or 30 ppm OxBC. Similarly, the average daily feed intake of birds was significantly improved (P=0.016) in birds fed 10, and 30 ppm OxBC over the grower period (days 18 to 31), but not in birds fed 5 ppm OxBC (see Table 4). This is despite a numerically higher feed intake in birds fed 5 ppm OxBC over this time period. No significant differences (P=0.486) were noted in mean feed intakes among treatments in the finisher phase (day 31-38), although they were numerically higher in birds fed OxBC. Pooling the data over the entire production cycle revealed a tendency (P=0.062) toward higher total average daily feed intake in birds fed 10 and 30 ppm OxBC, but not in those fed 5 ppm OxBC.

The average daily gain of birds was significantly (P=0.012) higher in birds fed 5, 10 and 30 ppm OxBC relative to control birds fed starter diets (days 0 to 18), as well as in the grower phase (P<0.0001; days 18 to 31), but not in the finisher phase (P=0.936; days 31 to 38) (see Table 4). Over the entire trial (days 0 to 38), birds fed 5, 10 or 30 ppm OxBC had significantly (P=0.008) higher average daily gains (4.3%, 4.1%, and 5.6%, respectively) relative to birds fed the unsupplemented control diet.

Dietary supplementation with OxBC significantly improved the mean final body weights of birds by 3.7% (5 ppm), 3.0% (10 ppm), and 4.3% (30 ppm) after 38 days of growth under normal rearing conditions. Average feed intakes tended to be improved, while average daily gains were significantly improved with OxBC dietary supplementation.

OTHER EMBODIMENTS

All publications and patent applications, and patents mentioned in this specification are herein incorporated by reference.

While the invention has been described in connection with specific embodiments, it will be understood that it is capable of further modifications. Therefore, this application is intended to cover any variations, uses, or adaptations of the invention that follow, in general, the principles of the invention, including departures from the present disclosure that come within known or customary practice within the art.

Other embodiments are within the claims.

What we claim is:

1. A foodstuff comprising from 0.00001% to 0.005% (w/w) oxidatively transformed carotenoid, wherein said oxidatively transformed carotenoid comprises a mixture, and wherein said mixture comprises a polymeric component formed by reaction of 6 to 8 molar equivalents of oxygen with a carotenoid.

2. The foodstuff of claim 1, wherein said foodstuff is a baked good, beverage, beverage mix, health bar, biscuit, or animal feed.

3. The foodstuff of claim 2, wherein said foodstuff is an animal feed and said animal feed is a dry or semi-moist pet food.

4. The foodstuff of claim 2, wherein said foodstuff is an animal feed.

5. The foodstuff of claim 2, wherein said foodstuff is a beverage mix and said beverage mix is a powder or a liquid concentrate.

6. The foodstuff of claim 1, wherein said foodstuff further comprises an antioxidant.

TABLE 4

|  | Average Daily Feed Intake (g/day) | | | | Average Daily Gain (g/day) | | | |
| --- | --- | --- | --- | --- | --- | --- | --- | --- |
|  | D 0-18 | D 18-31 | D 31-38 | D 0-38 | D 0-18 | D 18-31 | D 31-38 | D 0-38 |
| 0 ppm control | 41.3 | 125.0 | 195.0 | 96.9 | 27.9 | 70.9 | 89.4 | 53.1 |
| 5 ppm OxBC | 43.6 | 128.1 | 197.9 | 99.5 | 29.4 | 75.0 | 89.0 | 55.4 |
| 10 ppm OxBC | 43.4 | 132.0 | 197.4 | 100.5 | 29.6 | 74.4 | 89.0 | 55.3 |
| 30 ppm OxBC | 44.1 | 130.7 | 201.6 | 101.3 | 29.9 | 75.1 | 90.6 | 56.1 |
| P value | 0.001 | 0.016 | 0.486 | 0.062 | 0.012 | 0.000 | 0.936 | 0.008 |
| Pooled SEM | 0.4 | 1.5 | 3.0 | 1.1 | 0.4 | 0.7 | 2.1 | 0.6 |

7. The foodstuff of claim 1, wherein said foodstuff comprises from 0.00001% to 0.001% (w/w) oxidatively transformed carotenoid.

8. The foodstuff of claim 1, wherein said foodstuff comprises from 0.00001% to 0.0005% (w/w) oxidatively transformed carotenoid.

9. A method for making a foodstuff, said method comprising the step of mixing oxidatively transformed carotenoid with a foodstuff to form a foodstuff comprising from 0.00001% to 0.005% (w/w) oxidatively transformed carotenoid, wherein said oxidatively transformed carotenoid comprises a mixture, and wherein said mixture comprises a polymeric component formed by reaction of 6 to 8 molar equivalents of oxygen with a carotenoid.

10. The method of claim 9, wherein said foodstuff is an animal feed.

11. The foodstuff of claim 1, wherein said carotenoid is selected from the group consisting of lycopene, beta-carotene, zeaxanthin, echinenone, isozeaxanthin, astaxanthin, canthaxanthin, lutein, citranaxanthin, β-apo-8'-carotenic acid ethyl ester, alloxanthin, an apocarotenol, astacene, capsanthin, capsorubin, a carotenediol, a carotenetriol, a carotenol, cryptoxanthin, decaprenoxanthin, epilutein, fucoxanthin, a hydroxycarotenone, a hydroxyechinenone, hydroxylycopene, lycoxanthin, neurosporine, phytoene, phytofluoene, rhodopin, spheroidene, torulene, violaxanthin, apocarotenoic acid, β-apo-8'-carotenoic acid, azafrin, bixin, a carboxylcarotene, crocetin, diapocarotenoic acid, neurosporaxanthin, norbixin, and lycopenoic acid.

12. The foodstuff of claim 1, wherein said polymeric material has a molecular weight greater than 1,000 Daltons.

13. The foodstuff of claim 4, wherein said animal feed is horse feed.

14. The foodstuff of claim 4, wherein said animal feed is swine feed.

15. The foodstuff of claim 4, wherein said animal feed is poultry feed.

16. The foodstuff of claim 4, wherein said animal feed is sheep feed.

17. The foodstuff of claim 4, wherein said animal feed is cattle feed.

18. The foodstuff of claim 4, wherein said animal feed is fish feed.

19. The method of claim 9, wherein said carotenoid is selected from the group consisting of lycopene, beta-carotene, zeaxanthin, echinenone, isozeaxanthin, astaxanthin, canthaxanthin, lutein, citranaxanthin, β-apo-8'-carotenic acid ethyl ester, alloxanthin, an apocarotenol, astacene, capsanthin, capsorubin, a carotenediol, a carotenetriol, a carotenol, cryptoxanthin, decaprenoxanthin, epilutein, fucoxanthin, a hydroxycarotenone, a hydroxyechinenone, hydroxylycopene, lycoxanthin, neurosporine, phytoene, phytofluoene, rhodopin, spheroidene, torulene, violaxanthin, apocarotenoic acid, β-apo-8'-carotenoic acid, azafrin, bixin, a carboxylcarotene, crocetin, diapocarotenoic acid, neurosporaxanthin, norbixin, and lycopenoic acid.

20. The method of claim 9, wherein said polymeric material has a molecular weight greater than 1,000 Daltons.

21. The method of claim 10, wherein said animal feed is horse feed.

22. The method of claim 10, wherein said animal feed is swine feed.

23. The method of claim 10, wherein said animal feed is poultry feed.

24. The method of claim 10, wherein said animal feed is sheep feed.

25. The method of claim 10, wherein said animal feed is cattle feed.

26. The method of claim 10, wherein said animal feed is fish feed.

27. The method of claim 9, wherein said foodstuff comprises from 0.00001% to 0.001% (w/w) oxidatively transformed carotenoid.

28. The method of claim 9, wherein said foodstuff comprises from 0.00001% to 0.0005% (w/w) oxidatively transformed carotenoid.

* * * * *